United States Patent [19]
Hagedorn et al.

[11] Patent Number: 5,872,300
[45] Date of Patent: Feb. 16, 1999

[54] PROCESS FOR THE PREPARATION OF 2-AMINO-6-CHLOROPHENYL-ALKYLSULFANES, AND 2-AMINO-6-CHLOROPHENYL-ISOPROPYLSULFANE

[75] Inventors: Ferdinand Hagedorn, Leverkusen; Wolfgang Kiel, Odenthal; Helmut Fiege, Leverkusen, all of Germany

[73] Assignee: Bayer Aktiengesellschaft, Leverkusen, Germany

[21] Appl. No.: 749,129

[22] Filed: Nov. 14, 1996

[30] Foreign Application Priority Data

Nov. 22, 1995 [DE] Germany ............... 195 43 475.7

[51] Int. Cl.⁶ .................................................. C07C 209/36
[52] U.S. Cl. ..................... 564/417; 564/422; 564/423; 564/440
[58] Field of Search ................. 564/417, 422, 564/423, 440

[56] References Cited

U.S. PATENT DOCUMENTS

| | | | |
|---|---|---|---|
| 3,989,756 | 11/1976 | Fujise et al. | 260/580 |
| 4,059,627 | 11/1977 | Kritzler et al. | |
| 4,230,637 | 10/1980 | Zander | 260/580 |
| 4,808,752 | 2/1989 | Papenfuhs | |
| 5,105,011 | 4/1992 | Cordier et al. | 564/417 |
| 5,126,485 | 6/1992 | Bailliard et al. | |

FOREIGN PATENT DOCUMENTS

| | | |
|---|---|---|
| 0306222 | 3/1989 | European Pat. Off. |
| 0409709 | 1/1991 | European Pat. Off. |
| 1489916 | 11/1967 | France . |
| 2330669 | 6/1977 | France . |
| 3528033 | 2/1987 | Germany . |
| 1156005 | 6/1969 | United Kingdom . |
| 9611906 | 4/1996 | WIPO . |

OTHER PUBLICATIONS

J.M. Grosselin, et al., High Selectivities in Hydrogenation of Halogenonitrobenzenes on # Palladium, Platinum, or # Raney Nickel as Catalysts, Chem. Ind., (53), pp. 103–109, (1994).
CA125:114319r, Aug. 1996.
II. Farmaco, Ed. Sci. 12, pp. 206–217, (1957).
Bull. Chim. Soc. de France, 1951, Seiten 621–626, XP000616723, R. Specklin, et al.: *Tabelle IV, Verbindung 3; Seite 624, Spalte 2, Methode B*.
J. Heterocycl. Chem., Bd. 22, Nr. 5, (1985), Seiten 1345–1348, XP000616259, C. Corral, et al.: *Seite 1348, Spalte 1, Herstellung von Verbindungen 10a–d*.
J. Med. Chem., Bd 34, Nr. 2, (1991), Seiten 675–687, XP000616258, H. Inoue, et al.: *Seite 683, Spalte 1, Herstellung von Verbindung 7c*.
Tetrahedron, Bd. 20, Nr.2, (1964), Seiten 177–187, XP000616256, K. Pilgram, et al.: *Seite 177, Verbindung lle*.

Primary Examiner—Brian M. Burn
Attorney, Agent, or Firm—Sprung Kramer Schaefer & Briscoe

[57] ABSTRACT

2-Amino-6-chlorophenyl-alkylsulfanes are prepared in a particularly advantageous manner by hydrogenating 2-chloro-6-nitrophenyl-alkylsulfanes catalytically in the presence of a solvent without the addition of a further sulfur compound, and the novel compound 2-amino-6-chlorophenyl-isopropylsulfane is provided.

8 Claims, No Drawings

PROCESS FOR THE PREPARATION OF 2-AMINO-6-CHLOROPHENYL-ALKYLSULFANES, AND 2-AMINO-6-CHLOROPHENYL-ISOPROPYLSULFANE

The present invention relates to a process for the preparation of 2-amino-6-chlorophenyl-alkylsulfanes in high yields and selectivities, and to the novel compound 2-amino-6-chlorophenyl-isopropylsulfane.

Substituted anilinosulfanes are intermediate products for the preparation of plant protection agents (cf., for example, EP-A2-0 306 222).

It is known that chlorine-free 2-aminophenyl-n-propylsulfane can be prepared by catalytic reduction of 2-nitrophenyl-n-propylsulfane (cf. II. Farmaco, Ed. Sei. 12, 206 to 217 (1957)). However, the reaction conditions are unfavorable and the yields of about 75% are quite low.

Catalytic reduction of chlorine-substituted nitroaromatics often gives chlorine-substituted anilines in only relatively low selectivities, since chlorine is then also split off hydrogenolytically to form dechlorinated aniline (cf. Chem. Ind. 1994, (53), pages 103 to 109). According to EP-A1-0 409 709, the tendency toward chlorine being split off hydrogenolytically is reduced in this reaction by addition of sulfur compounds, for example thiourea. The addition of sulfur compounds of course leads to a further component in the reaction mixture, which makes working up thereof more complicated.

Not only chlorine substituents but also sulfane groups, which on principle can also be split off hydrogenolytically, are present in the starting materials for the process according to the invention. Reductions in selectivity and yield are therefore to be expected in the preparation of 2-amino-6-chlorophenyl-alkylsulfanes by catalytic hydrogenation due to chlorine atoms and/or sulfane groups being split off.

A process has now been found for the preparation of 2-amino-6-chlorophenyl-alkylsulfanes, which comprises hydrogenating 2-chloro-6-nitrophenyl-alkylsulfanes catalytically in the presence of a solvent without the addition of a further sulfur compound.

Compounds which can be employed in the process according to the invention are, for example, 2-chloro-6-nitrophenyl-alkylsulfanes of the formula (I)

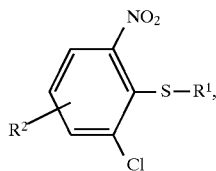

in which
$R^1$ represents $C_1$–$C_{18}$-alkyl, $C_3$–$C_8$-cycloalkyl or $C_7$–$C_{10}$-aralkyl and
$R^2$ represents hydrogen, $C_1$–$C_4$-alkyl, $C_1$–$C_4$-alkoxy or benzyl.

The corresponding 2-amino-6-chlorophenyl-alkylsulfanes of the formula

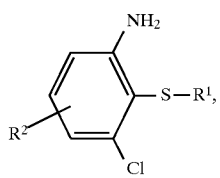

in which
$R^1$ and $R^2$ have the meaning given in the case of formula (I), are then obtained.

Alkyl and alkoxy groups can be straight-chain or branched. Cycloalkyl groups can optionally be substituted by $C_1$–$C_4$-alkyl.

Examples of alkyl groups are methyl, ethyl, propyl, isopropyl, butyl, isobutyl, tert-butyl, the isomeric amyls and the isomeric hexyls, octyls, decyls, dodecyls, heptadecyls and octadecyls.

Examples of $C_3$–$C_8$-cycloalkyl groups are cyclopropyl, cyclobutyl, cyclopentyl, cyclohexyl, cycloheptyl, cyclooctyl, methylcyclopropyl, dimethylcyclopropyl, methylcyclopentyl, dimethylcyclopentyl, methylcyclohexyl and dimethylcyclohexyl.

Examples of $C_7$–$C_{10}$-aralkyl groups are benzyl, α- and β-phenylethyl, phenylpropyl and phenylbutyl.

Examples of $C_1$–$C_4$-alkoxy groups are methoxy, ethoxy, propoxy, butoxy and isobutoxy.

Preferred alkyl groups are methyl, ethyl and isopropyl. Preferred cycloalkyl groups are cyclopropyl, cyclopentyl, cyclohexyl and the corresponding mono- and dimethylcycloalkyls. Preferred aralkyl groups are benzyl and phenylethyl. Preferred alkoxy groups are methoxy and ethoxy.

Particularly preferred starting substances are 2-chloro-6-nitrophenyl-methylsulfane, 2-chloro-6-nitrophenyl-ethylsulfane, 2-chloro-6-nitrophenyl-isopropylsulfane, 2-chloro-6-nitrophenyl-benzylsulfane and 2-chloro-6-nitrophenyl-cyclohexylsulfane.

The starting substances of the formula (I) are known from the literature or are accessible in a manner analogous to those known from the literature. In a particularly advantageous manner, 2-chloro-6-nitrophenyl-alkylsulfanes of the formula (I) can be obtained from the corresponding 2,3-dichloronitrobenzenes by reaction with a mercaptan of the formula (III)

$$H\text{—}S\text{—}R^1 \qquad (III),$$

in which
$R^1$ has the meaning given in the case of formula (I).

This reaction is carried out in the presence of a base, an aqueous medium and a phase transfer catalyst at 0° to 100° C. This process is the subject matter of an earlier patent application filed by the Applicant.

Possible solvents are, for example, alcohols and aromatics. The alcohols can be, for example, $C_1$–$C_6$-alkyl alcohols, and the aromatics can be, for example, $C_1$–$C_4$-alkylbenzenes. Methanol, ethanol, isopropanol, toluene and xylene are preferred. Solvent mixtures can also be employed, for example a methanol/toluene mixture.

The starting substances of the formula (I) can be in the form of a solution and/or suspension in the particular solvent.

Raney nickel is preferably used as the catalyst for the process according to the invention. The types Raney nickel 55 and Raney nickel 37-1 are particularly preferred. Alloys of Raney nickel, for example Raney nickel/iron or Raney nickel/cobalt, can also be employed.

The amount of catalyst can be varied within a wide range. For example, 0.5 to 25 g of catalyst can be employed per mol of nitro compound to be reduced, this weight data relating to moist catalyst material.

The process according to the invention can be carried out, for example, at temperatures between room temperature and 150° C. 20° to 120° C. are preferred. The pressure to be applied can be, for example, between normal pressure and 300 bar. 1 to 150 bar, in particular 2 to 100 bar, are preferred.

It is expedient to stir the mixture thoroughly while carrying out the process according to the invention.

The uptake of hydrogen has in general ended after 30 minutes to 5 hours. If appropriate, the reaction mixture can then be kept under the reaction conditions for a further period of time, for example 10 minutes to 1 hour. The reaction mixture can be worked up, for example, by cooling and releasing the pressure, separating off the catalyst, for example by filtration, rinsing it with solvent, combining the filtrates and removing the solvent from the filtrates, for example by stripping off in vacuo or by distillation. A product which is sufficiently pure for further use in most cases is then obtained. If appropriate, it can easily be obtained in purities of more than 99%, for example by distillation.

It is decidedly surprising that 2-amino-6-chlorophenyl-alkylsulfanes of the formula (I) can be obtained according to the invention in high yields and selectivities without the addition of sulfur compounds. Dehalogenations and desulfurizations take place to only a quite minor extent (in general below 0.5% in each case).

The present invention furthermore relates to the novel compound 2-amino-6-chlorophenyl-isopropylsulfane, which is accessible in the manner described above and can be used as an intermediate product for the preparation of plant protection agents.

EXAMPLES

The percentage data are percentages by weight, unless stated otherwise.

Example 1

34.7 g of 2-chloro-6-nitrophenyl-isopropylsulfane, 140.0 g of methanol and 1 g of Raney nickel 55, as the catalyst (water-moist), were initially introduced into a 0.3 l steel autoclave. After the air had been displaced with nitrogen and hydrogen, hydrogen was forced in at room temperature up to a pressure of 80 bar, while stirring the mixture, a slight increase in temperature already being observed. The mixture was heated to 60° C., while continuing to stir and keep the hydrogen pressure constant. After about 2 hours, the uptake of hydrogen had ended. The mixture was then cooled to room temperature, the hydrogen was let down, the catalyst was filtered off with suction and washed with methanol and the combined filtrates were concentrated. Crude yield: 29.6 g of 2-amino-6-chlorophenyl-isopropylsulfane with a purity of 99.5% (GC), corresponding to 97.5% of theory. The content of 2-isopropylmercaptoaniline formed by hydrogenating dehalogenation was only 0.1%. Furthermore, only 0.1% of impurities due to 3-chloroaniline, formed by hydrogenating desulfurization, were found.

Example 2

46.6 g of 2-chloro-6-nitrophenyl-isopropylsulfane, 160 ml of methanol and 5 g of Raney nickel 55 (water-moist, washed with methanol) were introduced into a steel autoclave. After flushing with nitrogen and hydrogen, the mixture was heated to 50° C., while stirring, and hydrogenation was carried out by forcing in hydrogen up to a maximum of 2 bar. After 2.5 hours, the uptake of hydrogen had ended. The mixture was then cooled to room temperature, the hydrogen was let down and the nickel catalyst was removed by filtration with suction and washed with methanol. After removal of the solvent, 39.9 g of 2-amino-6-chlorophenyl-isopropylsulfane were obtained in a purity of 97.8% (GC), which corresponds to 97% of theory. Only 0.2% of 2-aminophenylisopropylsulfane (formed by dehalogenation) was found as an impurity. Pure, colorless 2-amino-6-chlorophenyl-isopropylsulfane with a content of more than 99% was obtained by distillation at a boiling point of 144° C. at 11 mbar.

Example 3

40 g of 2-chloro-6-nitrophenyl-isopropylsulfane, 160 g of methanol and 2.4 g of Raney nickel 37-1 (methanol-moist) were initially introduced into a 0.7 l steel autoclave. After rinsing with nitrogen, 70 bar of hydrogen were forced in and the contents of the autoclave were heated to 100° C., while stirring. The hydrogen pressure was increased to 80 bar. After 50 minutes, the uptake of hydrogen had ended. The mixture was kept under the reaction conditions for a further 30 minutes. After cooling, letting down the hydrogen and removing the catalyst, the solvent was distilled off. Crude 2-amino-6-chlorophenyl-isopropylsulfane was already obtained as a 99% pure product (GC) which contained only 0.2% of 2-aminophenyl-isopropylsulfane (formed by dechlorination) and only 0.3% of m-chloroaniline (formed by desulfurization). The yield was 34.5 g.

We claim:

1. A process for the preparation of a 2-amino-6-chlorophenyl-alkylsulfane, which comprises hydrogenating a 2-chloro-6-nitrophenyl-alkylsulfane catalytically in the presence of a Raney nickel catalyst and a solvent, without the addition of a further sulfur compound.

2. The process as claimed in claim 1, wherein a 2-chloro-6-nitrophenyl-alkylsulfane of the formula (I)

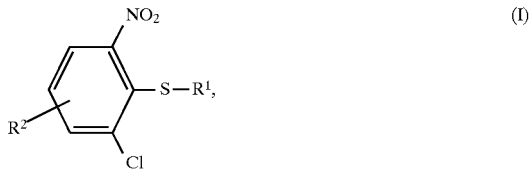

in which
$R^1$ represents $C_1$–$C_{18}$-alkyl, $C_3$–$C_8$-cycloalkyl or $C_7$–$C_{10}$-aralkyl and
$R^2$ represents hydrogen, $C_1$–$C_4$-alkyl, $C_1$–$C_4$-alkoxy or benzyl,
is employed, and a 2-amino-6-chlorophenyl-alkylsulfane of the formula

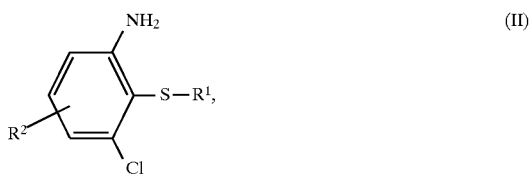

in which
$R^1$ and $R^2$ have the meaning given in the case of formula (I), is prepared.

3. The process as claimed in claim 1, wherein 2-chloro-6-nitrophenyl-methylsulfane, 2-chloro-6-nitrophenyl-ethylsulfane, 2-chloro-6-nitrophenyl-isopropylsulfane, 2-chloro-6-nitrophenyl-benzylsulfane or 2-chloro-6-nitrophenyl-cyclohexylsulfane is employed.

4. The process as claimed in claim 1, wherein an alcohol and/or aromatic is employed as the solvent.

5. The process as claimed in claim 1, wherein Raney nickel is employed as the catalyst.

6. The process as claimed in claim 1, which is carried out at a temperature between room temperature and 150° C.

7. The process as claimed in claim 1, which is carried out under a pressure of between normal pressure and 300 bar.

8. 2-Amino-6-chlorophenyl-isopropylsulfane.

* * * * *